(12) United States Patent
Sechrist et al.

(10) Patent No.: US 9,394,166 B1
(45) Date of Patent: Jul. 19, 2016

(54) INCREASED PLASMON RESONANCE FREQUENCY STABILITY DRAWN FROM A REFRACTIVE INDEX GRADIENT SPANNING NEGATIVE AND POSITIVE VALUES

(71) Applicants: Zachary A. Sechrist, Ridgecrest, CA (US); Ronald J. Tonucci, Waldorf, MD (US); Lee R. Cambrea, Ridgecrest, CA (US)

(72) Inventors: Zachary A. Sechrist, Ridgecrest, CA (US); Ronald J. Tonucci, Waldorf, MD (US); Lee R. Cambrea, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 921 days.

(21) Appl. No.: 13/622,841

(22) Filed: Sep. 19, 2012

Related U.S. Application Data

(60) Provisional application No. 61/602,996, filed on Feb. 24, 2012.

(51) Int. Cl.
*B82Y 15/00* (2011.01)
*B82Y 20/00* (2011.01)
*G02B 1/00* (2006.01)

(52) U.S. Cl.
CPC ............... *B82Y 15/00* (2013.01); *B82Y 20/00* (2013.01); *G02B 1/002* (2013.01)

(58) Field of Classification Search
CPC ........ B82Y 15/00; B82Y 20/00; B82Y 40/00; C40B 60/12; G01N 21/41; G01N 21/55; H01L 21/20; H01L 29/66; G02B 1/00; G02B 1/002–1/007; H01P 1/20–1/2005
USPC ....... 359/356; 506/39; 356/128, 445; 438/48; 257/467
See application file for complete search history.

(56) References Cited

U.S. PATENT DOCUMENTS

| | | | | |
|---|---|---|---|---|
| 4,981,778 | A * | 1/1991 | Brault | G03F 7/094 430/270.1 |
| 2004/0180379 | A1* | 9/2004 | Van Duyne | B82Y 15/00 435/7.1 |
| 2006/0267472 | A1* | 11/2006 | Blalock | H01J 1/304 313/336 |
| 2010/0253940 | A1* | 10/2010 | Xia | G01N 21/658 356/301 |
| 2012/0081687 | A1* | 4/2012 | Burrow | G02B 27/10 355/71 |

FOREIGN PATENT DOCUMENTS

WO    WO 2011/040923 A1 *   4/2011   ............... G01J 3/44

OTHER PUBLICATIONS

R. Tonucci & Z. Sechrist, The Effects of FIB Dwell Time on Ion Milling Submicron Diameter Holes in Au/Alumina and Au/MgF2 Multilayered Substrates for Metamaterial Applications, Poster at 4th Annual Washington, DC Focused Ion Beam User Group Meeting, Feb. 25, 2011, Baltimore, MD, USA.

* cited by examiner

*Primary Examiner* — Stephone B Allen
*Assistant Examiner* — Adam W Booher
(74) *Attorney, Agent, or Firm* — James M. Saunders

(57) ABSTRACT

An increased plasmon resonance frequency stability drawn from a refractive index gradient spanning negative and positive values includes a two-dimensional array of tapered nanowells. A multilayer of alternating materials is associated with the two-dimensional array of tapered nanowells. The multilayer of alternating materials are alternating layers of electrical conductors and electrical insulators.

7 Claims, 5 Drawing Sheets

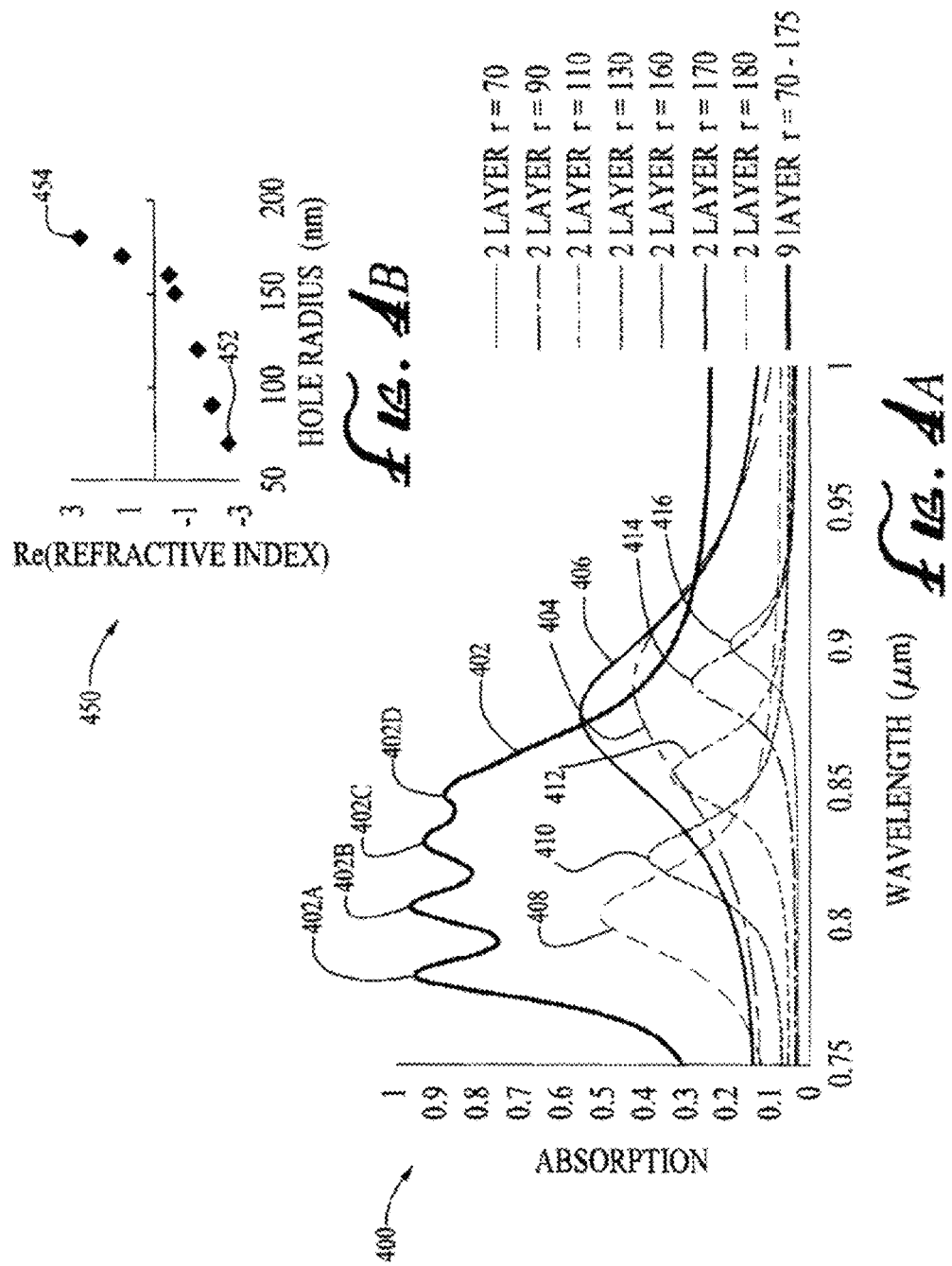

INCREASED PLASMON RESONANCE FREQUENCY STABILITY DRAWN FROM A REFRACTIVE INDEX GRADIENT SPANNING NEGATIVE AND POSITIVE VALUES

CROSS-REFERENCE TO RELATED APPLICATIONS

This is a non-provisional application, claiming the benefit of, parent provisional application No. 61/602,996 filed on Feb. 24, 2012, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

Embodiments of the invention generally relate to plasmonic surfaces, and more particularly, to plasmonic surfaces with small features that have an inherent insensitivity to varying size/shape of the features.

BRIEF DESCRIPTION OF THE DRAWINGS

FIG. 4A is a graphical representation of absorption spectra for various circular metal-insulator-metal (MIM) resonators with different radii and the spectra for a multilayered nanowell with radii spanning all of the MIM radii displayed, according to embodiments of the invention.

FIG. 4B is a graphical representation of real components for the complex refractive index, showing the negative and positive effective refractive indices at resonance for typical two-metal layer resonators, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

Embodiments of the invention generally relate to plasmonic surfaces, and more particularly, to plasmonic surfaces with small features that have an inherent insensitivity to varying size/shape of the features. Embodiments of the invention use a stack of plasmonic resonators with refractive indices ranging from negative to positive values.

A finite element solver was used to model a metamaterial structure that could produce a large and stable Raman scattering enhancement. The metamaterial was an array of tapered nanowells etched into a metal/dielectric multilayer stack. The plasmonic activity as a function of the number of layers and sidewall angle of the nanowell was investigated. As nanowell side wall angle was increased, the tops of the nanowells drew closer to one another. The close proximity greatly increased localized electric field intensity in comparison with nanohole models with void separations comparable to hole diameters. The larger side wall angle also created an effective refractive index gradient between the top and bottom of the nanowell which stabilized the resonant frequency with respect to variation in diameter and periodicity commonly encountered with nanofabrication. Nanowells etched into metal/dielectric stacks and solid metal films were compared, and the multilayer system showed higher electric field intensity and greater bandwidth. These aspects are crucial when high sensitivity is imperative to detection. Potential uses of embodiments of the invention include locating and identifying chemicals in environments that have, in the past, been very difficult to detect such as airborne molecules.

Although embodiments of the invention are described in considerable detail, including references to certain versions thereof, other versions are possible. Examples of other versions include performing alternate combinations and sequencing of the materials to optimize plasmon resonance frequency stability. Therefore, the spirit and scope of the appended claims should not be limited to the description of versions included herein.

Figure 1:
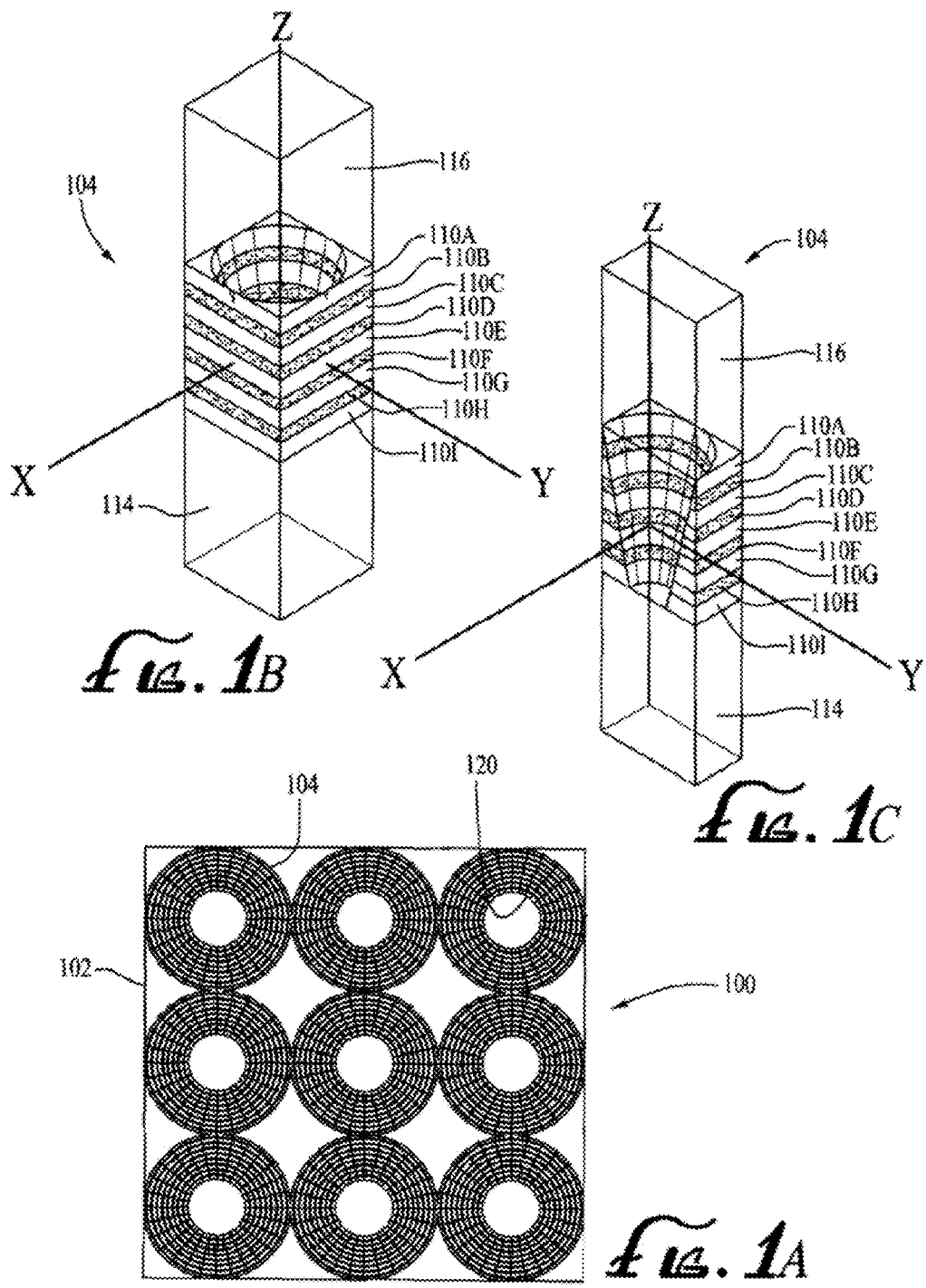
FIG. 1A is a plan view of a two-dimensional array of nanowells, according to embodiments of the invention.
FIG. 1B is a three-dimensional elevation view of a tapered nanowell etched into a metal/dielectric multilayer stack, according to embodiments of the invention.
FIG. 1C is a three-dimensional elevation view of a cross-section of a tapered nanowell etched into a metal/dielectric multilayer stack, according to embodiments of the invention.

In the accompanying drawings, like reference numbers indicate like elements. FIG. 1A illustrates a plan view of a two-dimensional array of nanowells, according to embodiments of the invention. FIG. 1B illustrates a three-dimensional elevation view of a tapered nanowell etched into a metal/dielectric multilayer stack, according to embodiments of the invention. FIG. 1C illustrates a three-dimensional elevation view of a section of a tapered nanowell etched into a metal/dielectric multilayer stack, according to embodiments of the invention. Reference character 100 depicts an apparatus of embodiments of the invention. The figures, including the elevation views depicted in FIGS. 1B and 1C, are drawn for ease of understanding and represent only one of many example materials that may be used in embodiments of the invention. Likewise, components may be referred to singularly or in pluralities, even though depicted as one or the other in the figures for simplified viewing, without detracting from the merits or embodiments of the invention.

Referring simultaneously to FIGS. 1A, 1B, and 1C, embodiments of the invention generally relate to a metamaterial structure, including: a two-dimensional array of tapered nanowells 102. The two-dimensional array of tapered nanowells 102 is a plurality of tapered nanowells 104 having a predetermined shape. A multilayer of alternating materials 110A through 110I is associated with the two-dimensional array of tapered nanowells 102. The multilayer of alternating materials 110A through 110I are alternating layers of electrical conductors and electrical insulators. Each tapered nanowell 104 is etched through the multilayer of alternating materials 110A through 110I. The predetermined shape of each nanowell 104 induces a gradient of hole diameters through the muhilayer of alternating materials 110A through 110I and perpendicular to the two-dimensional array of tapered nanowelis 102. The gradient of hole diameters generates a plurality of coupled resonators having effective refractive indices spanning both positive and negative values when isolated from the plurality of coupled resonators. When the plurality of coupled resonators includes individual resonators having both positive and negative effective refractive indices, plasmon resonance frequency stability of the metamaterial structure 100 is increased. Each of the individual resonators is a three layer sequentially oriented repeating metal-dielectric-metal stack having a unique refractive index defined by the gradient of hole diameters.

Each tapered nanowell 104 is a three-dimensional structure having an upper and lower border. The upper border is the top surface of the top most layer, shown as 110A in FIGS. 1B and 1C. The lower border is the bottom surface of the bottom most layer, shown as 110I in FIGS. 1B and 1C. An electric field is localized and has a maximized magnitude at the upper border. The upper border is the location of the narrowest gap between each tapered nanowell 104. Thus, the electric field is localized at the position at which the tapered nanowell 104 has the largest diameter, which is the upper limit of the top most layer, shown as 110A. The upper and lower borders are also commonly referred to as the upper and lower rims, without detracting from the merits or generality of the invention.

Each predetermined shape of each tapered nanowell 104 is based on application-specific conditions. Although depicted as circular in FIGS. 1A, 1B, and 1C, tapered nanowells 104 may be any shape such as, for example, circular, rectangular, square, angled, polygonal, or the compliment of any such structure, depending on application-specific conditions. A void 120 is formed in each layer of the multilayer of alternating materials when each tapered nanowell 104 is etched through the multilayer of alternating materials 110A through 110I. As depicted in FIGS. 1B and 1C, the multilayer of alternating materials 110A through 110I are arranged in a predetermined layered orientation.

The multilayer of alternating materials 110A through 110I may also be referred to as "multilayer strata of alternating materials" and "multilayer strata of alternating metal-dielectric films of nanometer scale thickness (or nanolaminate)" without detracting from the merits or generality of embodiments of the invention. Similarly, nanolaminates may be referred to as "multilayers of thin films," without detracting from the merits or generality of embodiments of the invention. Likewise, the tapered nanowell 104 may also be referred to as a "unit cell," without detracting from the merits or generality of embodiments of the invention. Furthermore, terms such as "plurality of resonators" may also be referred to as "plurality of coupled resonators," without detracting from the merits or generality of embodiments of the invention. Additionally, similar variations are possible such as, for example, referring to elements both singularly or in pluralities, without detracting from the merits or generality of embodiments of the invention.

Another embodiment of the invention generally relates to a metamaterial structure, including: a two-dimensional array of tapered nanowells 102. The two-dimensional array of tapered nanowells 102 is a plurality of tapered nanowells 104 having a predetermined shape. A multilayer strata of alternating metal-dielectric films 110A through 110I is associated with the two-dimensional array of tapered nanowells 102. The predetermined shape of each nanowell 104 induces a refractive index gradient through the multilayer strata of alternating metal-dielectric layers 110A through 110I and perpendicular to the two-dimensional array of tapered nanowells 102.

Each tapered nanowell 104 is a tapered circular hole cut through each layer of the multilayer strata of alternating metal-dielectric films 110A through 110I. Each tapered nanowell 104 has an upper and lower rim. An electric field is localized at the upper rim when the tapered nanowell 104 top rims are closer to nearest neighbors in the array 102 in comparison with the lower rim.

In yet another embodiment of the invention generally relates to a metamaterial structure, including: a two-dimensional array of tapered nanowells 102. The two-dimensional array of tapered nanowells 102 is a plurality of tapered nanowells 104 having a predetermined shape. A plurality of resonators 110A through 110I is associated with the plurality of tapered nanowells 104. The plurality of resonators 110A through 110I are alternating layers of electrical conductors and electrical insulators. The predetermined shape of each tapered nanowell 104 induces a refractive index gradient through the plurality of resonators 110A through 110I and perpendicular to the two-dimensional array of tapered nanowells 102. The refractive index gradient passes through a zero refractive index point, increasing plasmon resonance frequency stability of the metamaterial structure 100.

Each tapered nanowell 104 is a tapered circular hole cut through the plurality of resonators 110A through 110I. Each tapered nanowell 104 has an upper and lower rim. An electric field is localized and has a maximized magnitude at the upper rim. Each tapered nanowell 104 has a predetermined side wall angle. The predetermined side wall angle results in a larger diameter at an upper resonator associated with the plurality of resonators than a lower resonator associated with the plurality of resonators 110A through 110I.

In embodiments, the multilayer of alternating materials 110A through 110I is a plurality of resonators. Each resonator in the plurality of resonators 110A through 110I is a three layer sequentially oriented repeating metal-dielectric-metal stack. Each resonator in the plurality of resonators is bounded by an upper and lower insulator. An insulator is a dielectric layer. Each resonator in the plurality of resonators 110A through 110I displays effective refractive index spanning negative to positive values. The effective refractive index may also be referred to as effective index of refraction.

In embodiments, each tapered nanowell 104 has a predetermined side wall angle. The predetermined side wall angle results in a larger diameter at a top layer associated with the multilayer of alternating materials 110A through 110I than a bottom layer associated with the multilayer of alternating materials. Additionally, as diameters increase, the separation distance between tapered nanowells 104 is reduced. A selective material (not shown) is bound on the top layer to capture Raman active materials for sensing, composition identification, and discrimination.

In embodiments, each tapered nanowell 104 is a three-dimensional structure. The multilayer of alternating materials 110A through 110I are adhered to one another. An example of suitable adherence is a chemical bond.

In embodiments, the electrical conductors are metals selected from the group consisting of gold, silver, palladium, platinum, and aluminum. The metamaterial structure then operates in the energy regime from the visible through near infrared and infrared wavelengths. In other embodiments, the electrical conductors are metals selected from the group consisting of tungsten, platinum, and copper. The metamaterial structure then operates in the energy regime from the near infrared through the infrared wavelengths. The electrical insulators are dielectrics selected from the group consisting of polymers, rare earth oxides, metal oxides, metal nitrides, and metal fluorides.

In embodiments, the tapered nanowells 104 are on top of a substrate 114. The nanowells 104 stop at the glass substrate 114 and do not penetrate the substrate. The substrate 114 can be glass, a crystal, a polymer, semiconductor, or any number of dielectric materials. Glass is used in embodiments for economical reasons. A person having ordinary skill in the art will recognize that a substrate is the base on which a laminate is placed. The metamaterial (metal-dielectric nanolaminate with nanowells) is a structure on a substrate and is not acting as a substrate itself. For some applications, portions or all of the substrate 114 are removed leaving a supported or free standing nanolaminate with nanowells. Air 116 is above the nanowells 104.

The alternating layers 110A through 110I are alternating layers of electrical conductors and electrical insulators. The electrical conductor can be metal and the electrical insulator can be a dielectric. For operation in the visible through near infrared, suitable metals include gold, silver, and aluminum. For operation in the near infrared through infrared, other suitable metals can be tungsten, platinum, iridium, or copper. The dielectric can be alumina, magnesium fluoride, silica, polymer, europium oxide, a rare earth oxide, a metal oxide, or a metal fluoride. Magnesium fluoride is preferred in some embodiments because it is easily removed from the nanowell surface, when any has been redeposited during the ion milling process that creates the nanowells. Removal of the redeposited dielectric is preferred because it allows maximum exposure to the metal for attachment of SERS active materials such as benzenethiol. Alumina or aluminum oxide is more difficult to remove, however, because its higher permittivity allows the layers of dielectric to be thinner.

Surface enhanced Raman scattering (SERS) is one of the most studied plasmonic applications because of the unparalleled sensitivity and selectivity of the technique. Inelastic Raman scattering, an inherently insensitive process, can be enhanced by as much as $10^{14}$ through coupling between the molecule of interest and a plasmonic surface. The brunt of scientific research in the field has been focused on increasing the performance of the plasmonic surface. Two major thrusts for SERS surfaces have been the increase in the localized electric field strength, and the uniformity of the field across the surface. These two thrusts appear to compete with one another in experimental demonstrations, leading to the relationship known as the SERS Uncertainty Principle.

An approach for Raman enhancement has been a route of dispersion engineering through surface modification. By systematically adding or subtracting surface features, it is possible to tune the plasmonic resonances of the surface. Common types of modified surfaces are photonic crystals and metamaterials. By modifying the dispersion of the surface, it is possible to maximize the plasmonic activity at a select wavelength, thus maximizing the enhancement factors (EF) of the surface for a particular molecule. These surfaces are generally periodic structures, so the enhancement is uniformly distributed. The EF is not as high as for a hot spot on a random surface. It is understood in the art that a hot spot is a highly localized point of large field strength, giving rise to large Raman enhancement. The averaged EF is very similar between the two structures. These engineered lattices have strong nearest neighbor influences, which makes the average EF susceptible to disorder. Small inclusions of disorder greatly reduce the crystal performance. Disorder for nanoscale structures suitable for SERS is still highly probable. An error tolerant construction is therefore highly desirable.

Multilayer resonators show promise in the field of SERS. The U.S. Navy funded study associated with embodiments of the invention focuses on a multilayer resonator construction because of the excellent dispersion tunability of the system. The modeled material is similar to a three-dimensional fishnet structure but the rectangular holes are replaced with tapered circular holes that go through the metal/dielectric layers. Repeating unit cell construction distributes the electric field across the x,y-plane, effectively spreading the enhancement across the metamaterial surface to improve the signal uniformity.

Variation of the side wall angle was used to manipulate the surface plasmon activity. By increasing the side wall angle to the extent that the adjacent nanowells were almost touching, it was possible to explore the complement of nearly touching plasmonic spheres. The investigation into the electric field enhancement between two closely spaced spheres has been explored previously. In accordance with the Babinet principle, complementary metamaterials produce resonances at close to the same frequency and of similar strength. Therefore, since the closely spaced spheres produced a significant EF, one would also expect a high EF from a complementary void structure. Additionally, voids display strong plasmon confinement in comparison with spheres. This additional confinement may further enhance Raman scattering beyond the sphere test case.

A surface plasmon can occur at a metal/dielectric interface. The surface wave exists in both the metal and dielectric mediums. This plasmonic wave is therefore waveguided in both materials. In both cases, as the waveguide was reduced, the surface wave velocity was decreased. This negative wave acceleration reduced the propagating mode, and a leaky mode was increased. This led to a dramatic increase in the electric field intensity in that localized region—a hot spot. Once the nanowells overlapped, the top metal ring was discontinuous. In this case lower layers still closely resembled the high electric field enhancement from the closely spaced voids, while the top layer now mimicked the shape and function of a bowtie nanoantenna.

In both systems, nearly touching voids and bowtie nanoantennas, the electric field intensity was highest when their respective gaps were very small. This represented a problem as very small gaps are difficult to fabricate, and small variance could lead to a significant resonance frequency shift. The gap sensitivity is a perfect example of the SERS Uncertainty Principle, as the higher performance structure is more likely to have poor uniformity. The multilayer nanowell system was uniquely well adapted to overcome this problem. The multilayered nanowell with large side wall angle gave very large enhancements, but was stable with respect to potential fabrication errors due to coupling between progressively smaller effective refractive index resonators stacked on top of one another.

A commercially-available finite element solver was used to solve Maxwell's equations—High Frequency Structural Simulator (HFSS®) from Ansoft Corp. The three dimensional full wave electromagnetic solver was tested to validate the accuracy of the approach. Absorption was calculated from simulation scattering parameters, and related to the Raman intensity:

$$I_{SERS} \propto A(f_L) \cdot A(f_S), \text{ where:}$$

$A(f_L)$=Absorption at the excitation frequency $A(f_S)$=Absorption at the Raman shifted frequency One plasmonic resonance was used to interact with both frequencies, so the plasmon resonant frequency was tuned to occur between the excitation and Raman absorption frequencies. The excitation and Raman shift wavelengths were close, so the SERS intensity was roughly proportional to the square of the plasmon absorption. This simplified approach ignored the change in dielectric constant of the metal between the two frequencies and the electric field alignment relative to the molecular dipole, however the approach has been used to predict plasmonic activity in nanovoids previously.

In the case of benzenethiol, a common SERS analyte, the laser excitation was $\lambda$=785 nm, the Raman shift was 1073 cm$^{-1}$ ($\lambda$=857 nm), thus the target resonance was $\lambda$=821 nm or $f_P$=365 THz. The first order resonant peak position was optimized to occur at $\lambda$=821 nm by adjusting the periodicity and layer thicknesses. The first order resonant peak did not have as strong of an absorption as higher order resonances. However, the first order peak was more stable with respect to changes in the period and nanowell radius. Using the first order resonance also forced the array period to be smaller, allowing a higher nanowell packing density hot spots.

The modeled surface is shown in FIGS. 1B, and 1C. The substrate was glass with the real part of the dielectric constant $Re(\epsilon_{glass})$=235. The surrounding environment was assumed to be air $Re(\epsilon_{air})$=1. Layers 110B, 110D, 110F, and 110H are aluminum oxide, $Re(\epsilon_{Al2O3})$=2.72. The imaginary component of all three dielectric materials was assumed to be zero. Layers 110A, 110C, 110E, 110G, and 110I were gold, and were described by a complex dispersion relationship:

$$\varepsilon_{Au} = 1 - \frac{f_p^2}{f(f+i\Gamma)}$$

where:

$\epsilon_{Au}$=complex dielectric constant for gold $f_p$=plasma frequency=$2.1*10^{15}$ Hz $\Gamma$=scattering frequency=$1.9*10^{13}$ Hz The nanowells were arranged in a square lattice with a period of 345 nm. Incident radiation was polarized, with the electric field vector pointing in the y-direction, and the wave vector aligned with the surface normal. The alumina layers were 41 nm thick, and the gold layers were 60 nm thick. Optimization of the structure was performed using a quarter of the nanowell as the unit cell to expedite the process. Tapered nanowells all had a diameter at the bottom of the well of 140 nm, while the top of the wells were varied in diameter. The namwell construction assumes the well extends through all of the gold and alumina layers. Over etching into the substrate was examined. Over etching the well into the substrate shifted the resonance, but did not have deleterious effects of the strength or bandwidth of the plasmonic activity.

Figure 2:
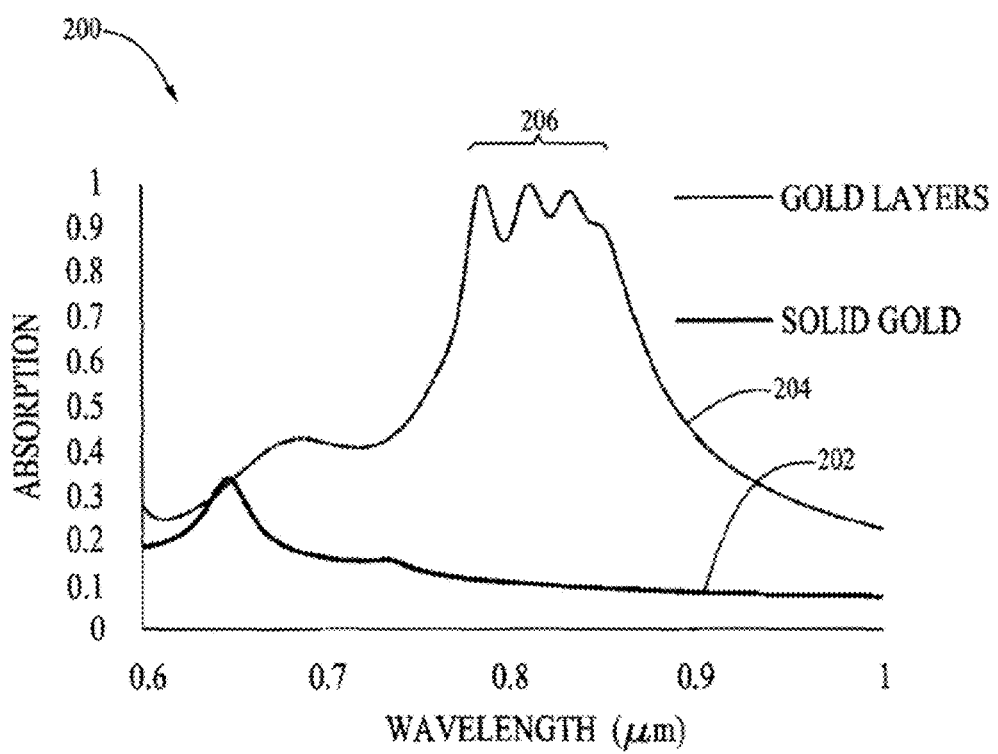
FIG. 2 is a graphical comparison of absorption spectra of identical geometry nanowells with one array etched into a solid gold film and the other array etched into a multilayered nanolaminate having nine gold layers, according to embodiments of the invention.

One of the most striking aspects to the nanowell construction was the use of multiple metal and dielectric layers. Solid and layered void arrays were compared. The simulated absorption spectra for identical geometry nanowells, one array etched into a solid gold film 202 and the other array etched into a multilayered nanolaminate having nine gold layers 204 (also referred to as a multilayer gold and alumina substrate), are compared in FIG. 2, depicted as reference character 200. Identical nanowell structures etched into the solid gold film 202 versus the multilayer gold and alumina nanolaminate 204 exhibited very different plasmonic responses. The multilayered sample 204 has nearly three times the peak absorption intensity, making the SERS intensity almost nine times higher. In addition, the peak 206 for the multilayered sample 204 is much broader. The wavelength position of the layered structure absorption peak was strongly red shifted compared to the solid well. The shift was attributed to plasmon coupling between the gold layers.

Although the difference between the spectra of layered metal and solid metal nanowells was quite dramatic, the difference in peak absorption intensity as a function of the number of layers was relatively low. The relative stability of the absorption strength stemmed from conflicting influences on the absorption strength. Adding layers would effectively increase the density of absorbers. Increasing the density of absorbers would clearly raise absorption. On the other hand, increasing the number of closely spaced gold layers can decrease total stack absorption due to destructive interference between the symmetric and anti-symmetric resonant modes. Therefore, increasing the number of layers can either increase or decrease the absorption depending on the relative strength of these two competing effects.

Figure 3A:
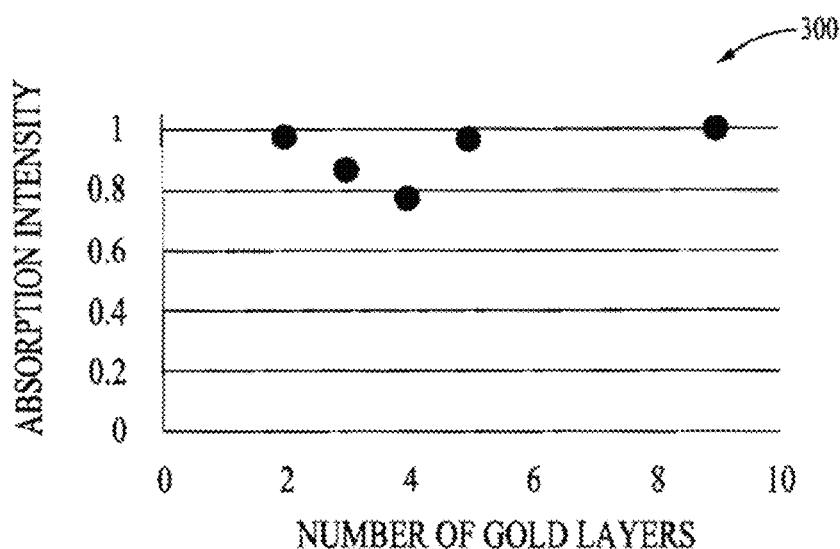
FIG. 3A is a graphical representation of absorption intensity as a function of the number of gold layers in a multilayer stack, according to embodiments of the invention.

Absorption as a function of the number of layers is shown in FIG. 3A, depicted as reference character 300. In simulations, each layer thickness was constant gold (Au)=60 nm and Aluminum Oxide (Al$_2$O$_3$)=41 nm. Each of the gold layers was separated by an alumina spacer layer. By adding gold layers, the total height of the nanowell stack was increased. The top and bottom radii of the tapered nanowell were held constant at 175 nm and 70 nm, respectively. The peak absorption intensity initially declined as the structure was tuned from two gold layers to three layers, and again decreased at four layers. When the fifth gold layer was added, the structure absorbed almost all of the light at the resonant frequency. As more layers were added, the peak absorption remained very strong (aba~1). Separating the nanowell further by decreasing the nanowell radius drastically reduced the absorption of the multilayers structures (not shown).

Figure 3B:
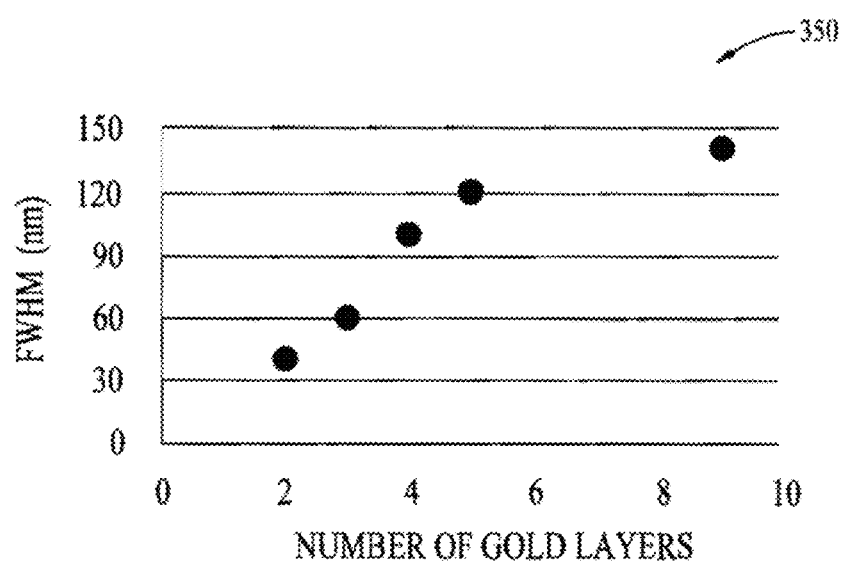
FIG. 3B is a graphical representation of the full wave half max of the absorption peak (bandwidth) as a function of the number of gold layers in a multilayer stack, according to embodiments of the invention.

FIG. 3B is a graphical representation of the full wave half max of the absorption peak (bandwidth) as a function of the number of gold layers in a multilayer stack, according to embodiments of the invention, and depicted as reference character 350. The breadth of the absorption peak was graphed in FIG. 3B as the full wave half max (FWHM) of the absorption peak. Although the sample absorption cannot be described as a Gaussian, nor any other simple curve shape, comparing the FWHM did represent the general peak broadening well. The absorption peak FWHM increased with the number of gold layers. The broader absorption peak extends the wavelength range which could excite, or be enhanced by, the surface plasmon. This extended range allowed a nanowell array surface to enhance scattering from analytes with a Raman absorption anywhere in the plasmonic range, and increased fabrication error tolerance towards a shift in the peak's spectral location. Since the sample with nine gold layers (and eight alumina layers) displayed excellent behavior, that sample was chosen as the target structure that would be optimized in simulations.

The increased absorption bandwidth displayed by the multilayered nanowell structure was attributed to both resonator coupling, and variable resonator geometries vertically stacked on top of one another. Each gold-alumina-gold sandwich represented an inductor-capacitor (LC) resonator. The nine gold layer stack had eight closely spaced LC resonators. The individual layers were coupled to each other through mutual inductance, and this coupling increased the individual resonator bandwidth. The close spacing of the nanowells also contributed to the large plasmonic bandwidth. As the plasmonic cavities approached each other, their localized electromagnetic field began to overlap. This overlap leads to higher field strength in the inter-cavity region, and a significant broadening of the resonant peak. The absorption peak broadening in a plasmonic array as a result of cavity expansion was expected and was clearly observed again in FIG. 3B.

FIG. 4A is a graphical representation of absorption spectra for various circular metal-insulator-metal (MIM) resonators with different radii and the spectra for a multilayered nanowell with radii spanning all of the MIM radii displayed, according to embodiments of the invention, and depicted as reference character 400. There was an additional contribution to the plasmon resonance broadening stemming from the additive nature of the eight vertically coupled LC resonators, each having a different resonance. The absorption spectra from arrays of individual LC resonators (two gold layers), and nine gold layers stacks with eight vertically coupled LC resonators is shown. The number of layers in the key represents the number of metal layers in the stack, each separated by an insulator layer. Curve 402 represents a nine gold layer nanowell with tapered circular holes etched out of the multilayer with radii ranging from 70 nm to 175 nm. Curves 404, 406, 408, 410, 412, 414, and 416 represent two gold layer nanowells with radii ranging from 180 nm to 70 nm.

The two gold layers resonators had the same diameter hole etched from the top and bottom gold plate. Adding the individual resonators together does not sum to the nine gold layers tapered nanowell spectra 402, but a comparison of the nine layers nanowell spectra and the individual resonators does lend insight into the additive role of the vertically stacked individual resonators towards the whole. The nine gold layers sample spectra 402 showed four peaks 402A, 4028, 402C, and 402D with shapes similar to the individual LC resonators, and the breadth of the nine layers sample absorption peak was comparable to the total bandwidth spanned by the series of individual LC resonators.

Embodiments of the invention are very unique because both blue shifting and red shifting are observed. To see both blue shifting and red shifting in the same structure while increasing the radius is very rare. A person having ordinary skill in the art will recognize that blue and red colors are at the opposite ends of the visible spectrum. Blue light is the highest energy, and shortest wavelength. Red is the lowest energy, and longest wavelength. When describing a change in wavelength position for an absorption (even outside the visible spectrum) spectroscopists use the terms blue shift or red shift to describe which direction the peak is moving on a graph with wavelength on the x-axis. To see both blue shifting and red shifting in the same structure while increasing the radius is very rare.

Upon closer inspection of the two gold layers resonator spectra, it was observed that the peak absorption first blue shifted with increasing hole radius. This effect was in direct contradiction to previous observations of isolated nanoholes with increasing radius. This contrary blue shift was attributed to the periodic composite of tapered nanowells acting as a plasmonic crystal. The plasmonic crystal behavior was determined by not only individual nanowell geometry, but also by the effective refractive index of the entire array. The increased well diameter was predicted to red shift the resonant wavelength due to increased cavity size, and nearest neighbor coupling effects. Counteracting the red shifting forces was a dramatic change in the effective refractive index as the nanowell diameter increased.

The two gold layers resonator creates an artificial magnetism that results in a negative permeability. The composite fishnet also had strong metal absorption, leading to a negative permittivity. This type of material has been labeled a double negative material because of these traits, and was characterized as a negative index metamaterial (NIM). The magnitude of the effective refractive index in the NIM was strongly tied to the resonator construct, thus small changes to the resonator construct led to significant changes in the effective refractive index.

The refractive index was de-embedded from HFSS scattering parameters. FIG. 4B shows the effective refractive index at resonance, depicted as reference character 450. The real part of the refractive index transitions from $-2.6$ (reference character 452) at nanowell top radius=70 nm to $+2.7$ (reference character 454) at nanowell top radius=180 nm, with a well to well spacing of 345 nm. As the refractive index goes from negative to positive, the absolute value of the real part of the refractive index gets smaller, and then larger. Assuming the plasmon resonance position was proportional to the absolute value of the refractive index, the peak position would blue shift and then red shift with increasing well diameter. Affirmation of this behavior in the two gold layers resonator simulations suggested that this plasmonic crystal effect was playing a major role in the position of the plasmonic resonance. There were additional factors to the effective dielectric of each resonator being overlooked by this simplified model, such as location within the stack and variation between the top and bottom layer hole diameter. The summation of these coupled resonators would lead to a broad absorption peak, as was observed.

In addition to bandwidth broadening, the combination of negative and positive effective refractive index resonators also gives the structure stability with respect to fabrication errors. The error tolerance between a nanowell with and without sidewall angle, made of metal/dielectric stacks and solid metal, wee compared to show the strength of the multilayer angled nanowell construction. The radii of the angled nanowell varied from 70 nm at the bottom, to 175 nm at the top. To maximize the intensity of the straight wall nanowell, the radius of all of the holes was held constant at 175 nm. Due to the variety of hole diameters, the structure with angle nanowell had more bandwidth. Absorption was greater than 85 percent for a wavelength range of 73 nm compared with only 25 nm for the straight wall nanowell. Error in the nanowell radius and array period were investigated, and shown in TABLE 1.

TABLE 1

Comparison of Wavelength Shift Experience in Nanowell Arrays Made With & Without Side Wall Angles, and Etched into a Solid or Multilayered Film.

| | 1.45% Period Change | 2.90% Period Change | 1.45% Radius Change | 2.90% Radius Change |
|---|---|---|---|---|
| Multilayer Straight Nanowell | 5.1% | 11.8% | 5.3% | 9.1% |
| Multilayer Angled Nanowell | 1.1% | 3.2% | 0.5% | 0.6% |
| Solid Gold Straight Nanowell | 4.1% | 7.1% | 2.1% | 4.6% |
| Solid Gold Angled Nanowell | 19.4% | 21.6% | 5.9% | 9.9% |

Error was calculated as the wavelength shift of the resonant absorption peak given a small change in the designated variable. A slight change in the peak location may not destroy the enhancement for a broad peak seen for the angled nanowell, but the shifts seen for straight wall nanowell would definitely move the resonant peak too far to couple to the targeted analyte. The wavelength shift stability was attributed to counter balancing red and blue shift forces of the angled nanowell. The tapered nanowell creates a hot spot that reaches a peak intensity when the nanowells were just barely overlapped, but remains present within the 4.5% error measured for the period and radius. All of the investigated structures became more stable to fabrication errors when the wells were spaced further apart, but the electric field intensity dropped off dramatically.

Figure 5:
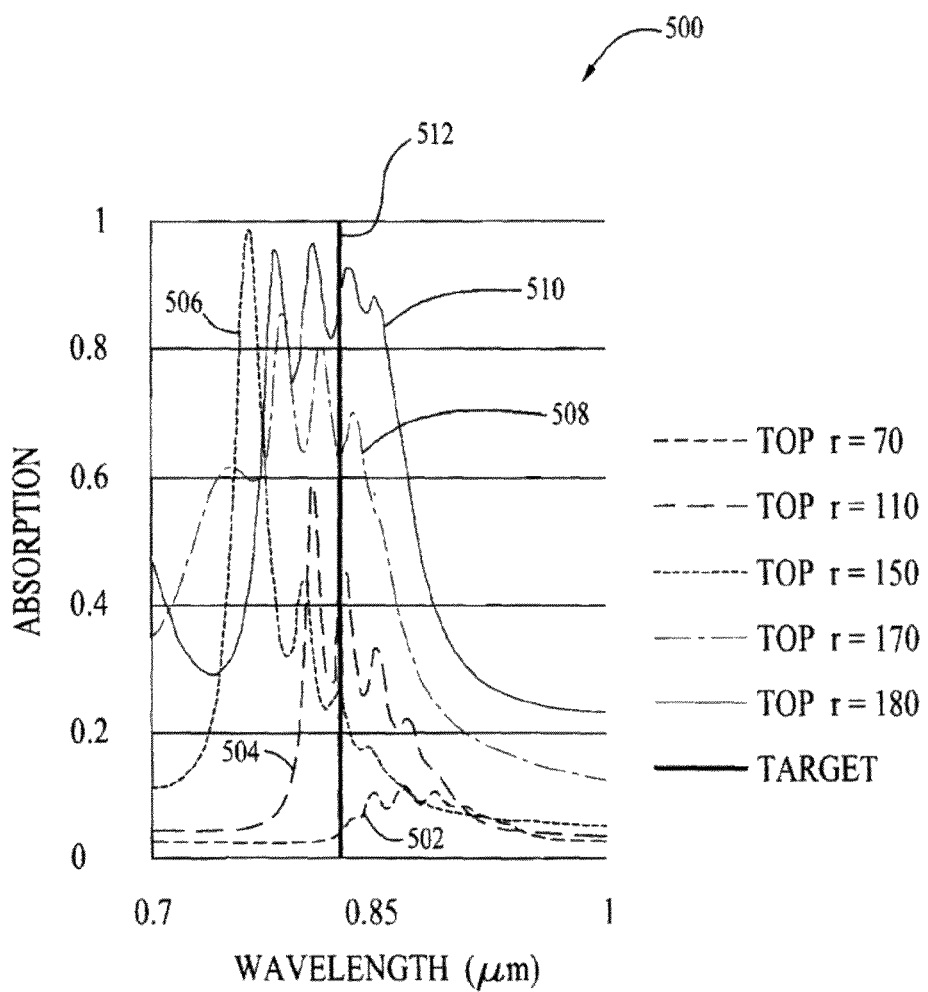
FIG. 5 is a graphical representation of absorption spectra of a nanowell etched into a nine gold layer stack with varying side wall angle, according to embodiments of the invention.

FIG. 5 is a graphical representation of absorption spectra of a nanowell etched into a nine gold layer stack with varying side wall angle, according to embodiments of the invention, and is depicted as reference character 500. The total absorption, and therefore SERS EF, increased with sidewall angle. The bottom radius of the tapered nanowells was held constant at 70 nm. As the top ring radius increased from 70 nm to 180 nm, the peak intensity grew from Abs=0.12-0.96 (depicted as curves 502, 504, 506, 508, and 510). A vertical line 512 represents the target absorption wavelength for benzenethiol. All structures shown were predicted to give some enhancement. The wavelength bandwidth of high absorption intensity increased with sidewall angle. The nanowell array period was 345 nm, so the nanowell with a top radius=170 nm 508 was almost overlapped with its nearest neighbors. The nanowell with a top radius=180 nm 510 was overlapped with its nearest neighbors. Curve 510 has greatest absorption intensity at the target absorption wavelength 512. Thus, it can be seen that slight overlap improves surface performance. The frequency shift in the layered structure with varying sidewall angle was minimal. This relative stability stems from the bottom layers being blue shifted, as the top layers were red shifting. Such stability is useful in modeling nanostructures due to the high risk of error in nanofabrication.

The electric field enhancement from a nanowell array etched into a metal dielectric multilayer was investigated. The structure produced significant electric field activity as the nanowells in the array approached one another. Thus, the construction should produce very high Raman enhancement. Using multiple metal layers distributed the electric field in the z-direction, and broadened the enhancement bandwidth via layer coupling. The plasmonic absorption of a multilayered nanowell was three times stronger than a solid gold well. The side wall angle of the nanowell was varied, and larger side wall angle devices produced a strong resonator with a resonance wavelength position that was more resilient to fabrication imperfections. The wavelength stability of the large side wall angle nanowell was attributed to resonators at the top and bottom of the nanowell having conflicting responses to radius changes. This led to the nanowell spectral response having more stability than the solid gold structure, or the multilayer structure without side wall angle.

Another embodiment of the invention relates to a method of making a surface enhanced Raman scattering sensor, including: providing a substrate 114 having a flat surface. A multilayer metal-dielectric stack is fabricated by depositing alternating conductor-insulator layers on the flat surface of the substrate 114. A gallium focused ion beam is used to pattern an array of tapered nanowells into the multilayer metal-dielectric stack. Each of the tapered nanowells has predetermined side wall angles resulting in larger nanowell diameters at a top layer associated with the multilayer metal-dielectric stack than a bottom layer associated with the multilayer metal stack.

An acid dip is provided. The acid dip is used to remove re-deposited dielectric material resulting from the patterning of the array of tapered nanowells. A selective binding material is then applied to the top layer to capture and discriminate between potential Raman active adsorbates.

Fabrication of the metamaterial structure can be accomplished as follows. First, a multilayer metal-dielectric stack is fabricated on a face of a substrate by thermal evaporation, physical deposition, atomic layer deposition, chemical vapor deposition, or other methods. The layer thicknesses are much less than the SERS resonant wavelength. Next, a gallium focused ion beam is used to pattern an array of tapered nanowells in the stack. Subsequently, redeposited dielectric material may be removed by an acid dip. The magnesium fluoride dielectric is much easier to remove than aluminum oxide. A thin dielectric protective layer such as aluminum oxide, approximately one nanometer thick, can be applied to the surface of the nanowell array structure to extend the useful life of the upper metal surface from unintentional contamination A focused ion beam apparatus used for sputter patterning the multilayer stack can use as the sputtering ion Ga, Au, other metals, nobel gases or other ions to maximize sputter yield and minimize defect or re-deposition during the tapered nanowell fabrication process. A layer of benzenethiol or europium oxide can be deposited on the tapered nanowell array at the upper surface where the nanowell openings are widest. The electric field will be the greatest at this location, as discussed above. Other SERS active materials can also be deposited at this upper surface for materials characterization or sensing of gasses and particulates such as, for example, explosives. Surface selective materials can also be added to the upper surface of the pattered nanowells to bind SERS active materials for characterization and sensing. The surface selective materials can be based on chemical functionality, chemical reactivity, chirality, or size including nanoparticles or other materials used to attach SERS active materials.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A metamaterial structure, comprising:
   a two-dimensional array of tapered nanowells, wherein said two-dimensional array of tapered nanowells is a plurality of tapered nanowells having a predetermined shape;
   a multilayer of alternating materials associated with said two-dimensional array of tapered nanowells, wherein said multilayer of alternating materials are alternating layers of electrical conductors and electrical insulators, wherein each of said tapered nanowell is etched through said multilayer of alternating materials, wherein said multilayer of alternating materials is an alternating gold-alumina-gold stack comprising nine gold layers and eight alumina layers, wherein each gold layer in said alternating gold-alumina-gold stack is 60 nm thick, wherein each alumina layer in said alternating gold-alumina-gold stack is 41 nm thick;

wherein said predetermined shape of each of said tapered nanowell induces a gradient of hole diameters through said multilayer of alternating materials and perpendicular to said two-dimensional array of tapered nanowells;

wherein each of said tapered nanowell is a three-dimensional structure having an upper and lower border, wherein said upper border is parallel with said lower border, said upper border having a radius greater than said lower border;

wherein said gradient of hole diameters generates a plurality of coupled resonators having effective refractive indices spanning both positive and negative values when isolated from said plurality of coupled resonators;

wherein when said plurality of coupled resonators includes individual resonators having both positive and negative effective refractive indices, plasmon resonance frequency stability of said metamaterial structure is increased.

2. The metamaterial structure according to claim 1, wherein an electric field having a maximized magnitude is localized at said upper border, wherein said upper border is the location of the narrowest gap between each of said tapered nanowell.

3. The metamaterial structure according to claim 1, wherein each of said individual resonators is a three layer sequentially oriented repeating metal-dielectric-metal stack having a unique refractive index defined by said gradient of hole diameters.

4. The metamaterial structure according to claim 1, wherein a void is formed in each layer of said multilayer of alternating materials, wherein said void is located in the interior of each of said tapered nanowell when each of said tapered nanowell is etched through said multilayer of alternating materials, wherein said electric field is distributed in the z-direction through said multilayer of alternating materials and enhancement bandwidth is broadened by layer coupling.

5. The metamaterial structure according to claim 1, wherein each of said tapered nanowell has a predetermined side wall angle, wherein said predetermined side wall angle results in a larger diameter at a top layer associated with said multilayer of alternating materials than a bottom layer associated with said multilayer of alternating materials, wherein a selective material is bound on said top layer to capture Raman active materials for sensing, composition identification, and discrimination.

6. The metamaterial structure according to claim 1, wherein said lower border having a radius of 70 nm and said upper border having a radius of 175 nm.

7. The metamaterial structure according to claim 1, wherein said predetermined shape of each of said tapered nanowell is selected from the group of shapes consisting of circular, rectangular, square, angled, and polygonal.

* * * * *